United States Patent [19]

Enjoji et al.

[11] Patent Number: 4,807,634
[45] Date of Patent: Feb. 28, 1989

[54] MECHANICAL TYPE ULTRASONIC SCANNER

[75] Inventors: Susumu Enjoji, Ootawara; Yushichi Kikuchi, Tochigi; Kiyoshi Hara, Ootawara, all of Japan

[73] Assignee: Kabushiki Kaisha Toshiba, Kawasaki, Japan

[21] Appl. No.: 10,341

[22] Filed: Feb. 3, 1987

[30] Foreign Application Priority Data

Feb. 4, 1986 [JP] Japan .................... 61-21166
Feb. 28, 1986 [JP] Japan .................... 61-43673

[51] Int. Cl.$^4$ ............................ A61B 10/00
[52] U.S. Cl. ............................ 128/660.01
[58] Field of Search ............... 128/660, 661, 618–620, 128/629; 367/140

[56] References Cited

U.S. PATENT DOCUMENTS

| 4,316,271 | 2/1982 | Evert | 367/140 |
|---|---|---|---|
| 4,418,698 | 12/1983 | Dory | 128/660 |
| 4,424,813 | 1/1984 | Havlice et al. | 128/660 |
| 4,432,371 | 2/1984 | McAusland | 128/660 |
| 4,517,985 | 5/1985 | Teslowski et al. | 128/660 |
| 4,558,706 | 12/1985 | Nakada et al. | 128/660 |
| 4,567,895 | 2/1986 | Putzke | 128/660 |
| 4,601,292 | 7/1986 | Fidel et al. | 128/660 |

OTHER PUBLICATIONS

Gardiner, B. G. "Low Pressure Fluid-Filled UTS Transmission Chamber", Europ. Pat Appln No. 0089 131 published 21-09-83, FIG. 1 only.

Primary Examiner—Francis J. Jaworski
Attorney, Agent, or Firm—Cushman, Darby & Cushman

[57] ABSTRACT

A mechanical type ultrasonic scanner has a housing which includes an insertion hole and a window member. The window member possesses ultrasonic transmission properties. The housing is filled with an acoustic liquid medium. A vibrator and a scanning mechanism are also accommodated in the housing. The vibrator generates ultrasonic waves. The scanning mechanism mechanically moves the vibrator, to scan the ultrasonic waves generated thereby. A rotating shaft is inserted in the housing, through the insertion hole. The rotating shaft transmits the driving force of a motor to a scanning mechanism. A seal member is inserted between the housing and the rotating shaft in the insertion hole. A partition wall is formed in the housing, to partition it into a first liquid medium chamber and an adjacent second liquid medium chamber. The first liquid medium chamber accommodates the vibrator and the scanning mechanism. The partition wall guides bubbles, undesirably inserted into the acoustic liquid medium, from the first liquid medium chamber to the second liquid medium chamber, and prevents the bubbles from returning to the first liquid medium chamber.

7 Claims, 6 Drawing Sheets

F I G. 3
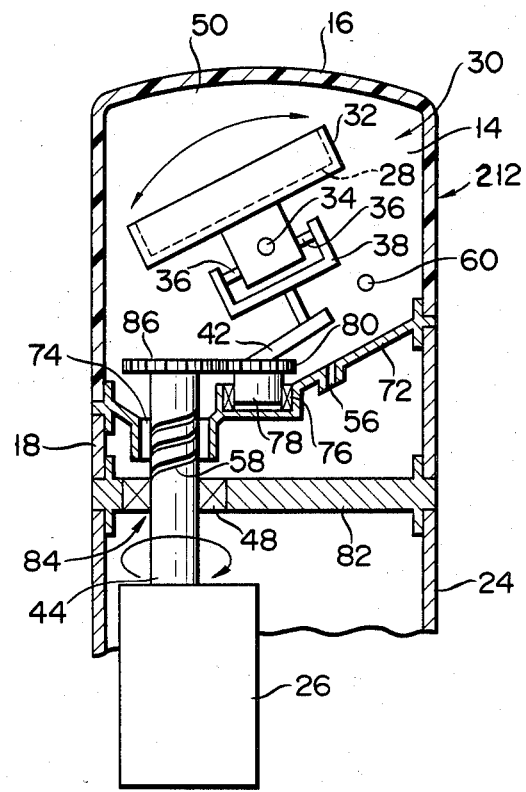

MECHANICAL TYPE ULTRASONIC SCANNER

BACKGROUND OF THE INVENTION

The present invention relates to a mechanical type ultrasonic scanner for mechanically swinging or rotating an ultrasonic vibrator to scan ultrasonic waves.

In such a mechanical type ultrasonic scanner, an ultrasonic vibrator is mechanically swept back and forth, or rotated to transmit ultrasonic waves onto a living organism to be examined, or receive them therefrom, thus obtaining ultrasonic information relating to the organism.

An operating vibrator in a conventional mechanical type ultrasonic scanner cannot be directly brought into contact with the subject to be examined. For this reason, as is shown in FIG. 1, a portion of the mechanical type ultrasonic scanner which is brought into contact with the skin of the patient is covered with plastic or by rubber window member 2. Vibrator 4 is arranged inside window member 2.

With the particular frequency range used to acquire ultrasonic information, it is difficult to transmit an ultrasonic wave if air is present between the vibrator and the skin of the patient. Therefore, liquid (acoustic medium) 6 which allows efficient propagation of the ultrasonic wave is poured into, and fills the space enclosed by window member 2.

In a conventional mechanical type ultrasonic scanner of this type, the rotational motion of a motor (not shown) must be converted into a swinging motion, by use of link mechanism 8 or the like, so as to sweep vibrator 4 back and forth. Unless the motor is completely immersed in liquid 6, liquid 6 will flow out, or bubbles will form between oil seal 11 and shaft 10 directly coupled to the motor. Formation of bubbles in liquid 6 degrades the ultrasonic image. Therefore, the bubbles formed in liquid 6 must be removed by some means or other, and subsequent formation of bubbles must also be retarded.

In the conventional scanner, liquid 6 generates a positive pressure in the space enclosed by window member 2, in order to prevent formation of bubbles or to remove bubbles from liquid 6 itself. In order to pour liquid 6 inside window member 2, a plug must be opened and then closed. The opening and closing of this plug is a rather cumbersome process. In addition, even window member 2 is filled with liquid 6, it is difficult to maintain a sufficiently high positive pressure therein.

SUMMARY OF THE INVENTION

It is an object of the present invention to provide a mechanical type ultrasonic scanner capable of simplifying the elimination of bubbles from an acoustic liquid medium.

According to an aspect of the present invention, there is provided a mechanical type ultrasonic scanner comprising:

a housing including an insertion hole and an ultrasonic transmission portion having ultrasonic transmission properties;

an acoustic liquid medium used to fill the housing;

wave-generating means, arranged in the housing, for generating an ultrasonic wave;

scanning means, also arranged in the housing, for mechanically moving the wave-generating means, to scan the ultrasonic wave generated thereby;

driving-force transmitting means, inserted into the housing, through the insertion hole, for transmitting a driving force to the scanning means;

seal means for sealing that portion of the insertion hole between the housing and the driving-force transmitting means; and bubble-trapping means for partitioning the housing into a first liquid medium chamber for accommodating the wave-generating means and the scanning means, and a second liquid medium chamber adjacent to the first liquid medium chamber, the bubble-trapping means being adapted to guide bubbles, undesirably inserted into the acoustic liquid medium, from the first liquid medium chamber to the second liquid medium chamber, and to prevent the bubbles from returning to the first liquid medium chamber.

The mechanical type ultrasonic scanner is brought into contact with the subject to be examined, such that an ultrasonic radiation surface is aligned in the vertical direction. The first acoustic liquid medium chamber with the scanning means therein is located below the second acoustic liquid medium chamber when in such an alignment position.

When the mechanical type ultrasonic scanner is used, bubbles formed in the first acoustic liquid medium chamber are moved upward by buoyancy, and are guided by a bubble-trapping means into the second acoustic liquid medium chamber.

The bubbles guided into the second acoustic liquid medium chamber are moved further upward and thus reach the inner wall surface of the chamber. In this way, the bubbles in the second acoustic liquid medium chamber are trapped by the bubble-trapping means. Even if the apparatus is rotated, the bubbles will not return to the first acoustic liquid medium chamber.

Since the bubbles in the first acoustic liquid medium chamber can be automatically eliminated while the apparatus is in use, a complicated air-elimination process need not be performed, unlike in the conventional mechanical type ultrasonic scanner.

BRIEF DESCRIPTION OF THE DRAWINGS

FIG. 3 is a sectional view showing a mechanical type ultrasonic scanner according to a second embodiment of the present invention;

FIGS. 4 and 5 show a mechanical type ultrasonic scanner according to a third embodiment of the present invention, in which FIG. 4 is a sectional view thereof, and FIG. 5 is a view showing the positional relationship between a motor and a vibrator;

FIGS. 6 to 8 are views showing a mechanical type ultrasonic scanner according to a fourth embodiment of the present invention, in which FIG. 6 is a sectional view thereof, FIG. 7 is a partially cutaway side view thereof, and FIG. 8 is an exploded perspective view thereof.

DETAILED DESCRIPTION OF THE PREFERRED EMBODIMENTS

A first embodiment of the present invention will now be described, with reference to FIG. 2.

Figure 1:
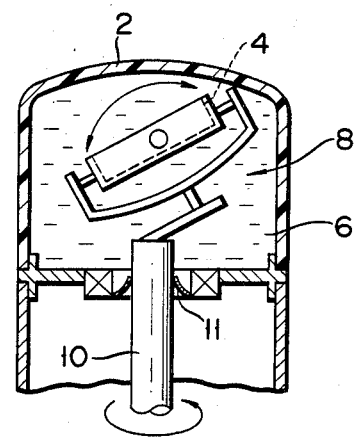
FIG. 1 is a sectional view showing a conventional mechanical type ultrasonic scanner.
Figure 2:
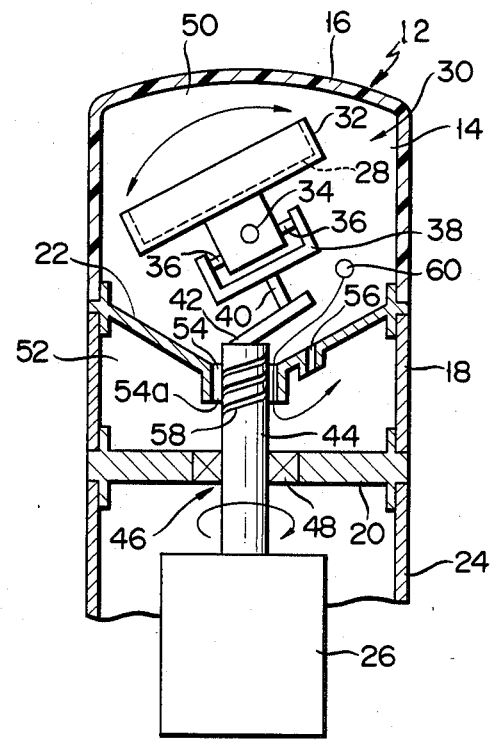
FIG. 2 is a sectional view showing a mechanical type ultrasonic scanner according to a first embodiment of the present invention.

Referring to FIG. 2, reference numeral 12 denotes a housing filled with acoustic liquid medium 14 such as water or glycol. Housing 12 includes window member 16, cylinder 18, and frame 20. Window member 16 comprises a plastic or rubber cylindrical member, open at one end. Window member 16 possesses ultrasonic transmission properties, and is brought into direct contact with the subject to be examined (i.e., the patient). One end of cylinder 18 engages with the open end of window member 16, by way of partition wall 22 (to be described later). Frame 20 is attached to the other end (i.e., side opposite to window member 16) of cylinder 18. Reference numeral 24 denotes a case which accommodates motor 26 and the like. Case 24 is attached to the other end of cylinder 18, by way frame 20.

Vibrator 28 and scan mechanism 30 are arranged inside housing 12. Vibrator 28 generates ultrasonic waves, and is connected to a lead wire (not shown). The lead wire provides ultrasonic pulses to vibrator 28 and echo signals from vibrator 28 to an ultrasonic imaging apparatus. Scanning mechanism 30 includes holder 32 for holding vibrator 28. Two pairs of radial support shafts 34 and 36 extend from holder 32. One pair of support shafts 34 are pivotally supported by a support frame (not shown) extending from partition wall 22 (to be described later). The other pair of support shafts 36 are pivotally supported by opposite ends of substantially U-shaped support arm 38. Rod 40 extends from the central portion of arm 38. The distal end of rod 40 is connected to connecting member 42, by means of a ball bearing (not shown). Connecting member 42 is connected to rotating shaft 44 of motor 26. When motor 26 is rotated, holder 32 is pivotally reciprocated about support shaft 34.

Rotating shaft 44 of motor 26 is inserted in housing 12, through insertion hole 46 formed in frame 20. Shaft 44 extends along the axis of window member 16. Seal member 48 is mounted in hole 46 in frame 20. Seal member 48 serves to seal a circular gap between frame 20 and rotating shaft 44 in hole 46.

Partition wall 22 is situated in housing 12 as to define first liquid medium chamber 50 and second liquid medium chamber 52. Chamber 50 accommodates vibrator 28, scanning mechanism 30, and the like. Chamber 52 is adjacent to chamber 50. More specifically, partition wall 22 has a funnel-shaped inner wall surface which is tapered toward chamber 52, that is to say, partition wall 22 has a portion, nearer central hole 54 thereof, which is separated more from vibrator 28. Window member 16 and cylinder 18 are coupled to the periphery of partition wall 22. The distal end portion of rotating shaft 44 is loosely inserted in central hole 54 of partition wall 22. Through hole 56 is formed in wall 22, between central hole 54 and the periphery of wall 22. Hole 56, together with a circular gap between hole-formation surface 54a and rotating shaft 44, constitutes a circulation path of acoustic liquid medium 14. More specifically, medium 14 flows, through the gap, from chamber 50 to chamber 52 and, at the same time, from chamber 52 to chamber 50, via through hole 56. Spiral groove 58 is formed in the peripheral surface of rotating shaft 44, at a position opposite to surface 54a.

The operation of the mechanical type ultrasonic scanner having the above arrangement will be described below.

A patient, as the subject to be examined, lies on a bed. The ultrasonic radiation surface, i.e., window member 16, is directed in the vertical direction and ultrasonic waves are generated by vibrator 28, while it is being reciprocated by motor 26, thereby enabling vibrator 28, and thus the scanner, to acquire ultrasonic information. With the mechanical scanner in this alignment position, first liquid medium chamber 50 is situated below second liquid medium chamber 52. Any bubbles 60 present in acoustic liquid medium 14 in chamber 50 are urged upward by buoyancy, and are guided along the surface of partition wall 22. Bubbles 60 then arrive near central hole 54, where buoyancy enables them to pass through the circular gap between rotating shaft 44 and hole-formation surface 54a of wall 22. If rotating shaft 44 of motor 26 is rotated, bubbles 60 are forcibly introduced into chamber 52, along spiral groove 58. Medium 14, together with bubbles 60, flows into chamber 52, and simultaneously, medium 14 in chamber 52 flows through hole 56, into chamber 50. Bubbles 60 continue to move upward and soon arrive near seal member 48. Even if the scanner is turned through 180 degrees, bubbles 60 in chamber 52 remain trapped at the corner of partition wall 22. Thus, for as long as the scanner continues its normal operations, bubbles 60 in chamber 52 will not return into chamber 50.

With the above arrangement, since any bubbles 60 in chamber 50 can be removed into, and then trapped in second liquid medium chamber 52, a complicated air elimination process is not required. In addition, spiral groove 58 is formed in the peripheral surface of rotating shaft 44, and holes 54 and 56 together with groove 58 constitute the circulating path of acoustic liquid medium 14. Bubbles 60 in chamber 56 can thus be smoothly transferred into chamber 52.

It should be noted that through hole 56 and central hole 54 need not be formed. Even in such a case, the unwanted bubbles can still be trapped. Hole 46, in which shaft 44 of motor 26 is inserted, can be cut in that wall of housing 12 which forms first liquid medium chamber 50.

A second embodiment of the present invention will now be described, with reference to FIG. 3. The same reference numerals as in FIG. 2 denote the same parts in FIG. 3, and a detailed description thereof will therefore be omitted.

In FIG. 3, reference numeral 72 denotes a funnel-shaped partition wall having hole 74 located at a position off from the center thereof. Bearing 76 is arranged on partition wall 72, along the axis of window member 16. Rotating shaft 78 is supported by bearing 76. Connecting member 42 is fixed to rotating shaft 78, and gear 80 is integrally mounted on shaft 78. Reference numeral 82 denotes a frame. Hole 84 for receiving rotating shaft 44 of motor 26 is formed in frame 82, at a position corresponding to hole 74. Gear 86 is integrally formed with rotating shaft 44 of motor 26. Gear 86 is meshed with gear 80.

The same effect as in the first embodiment can be obtained in the second embodiment having the structure as described above.

A third embodiment of the present invention will now be described, with reference to FIGS. 4 and 5.

Figure 4:
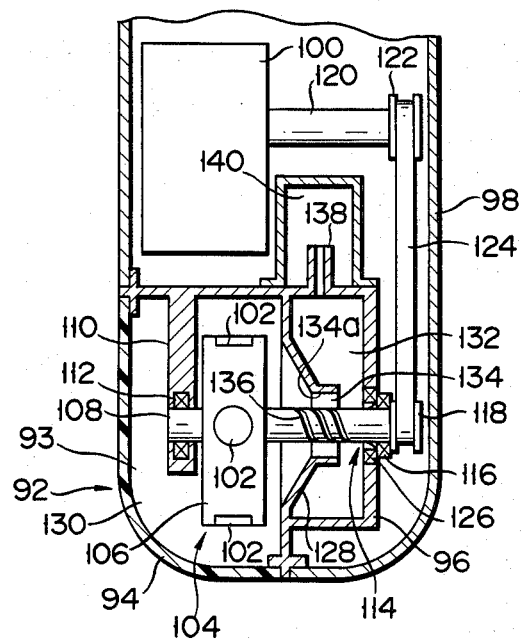
Figure 5:
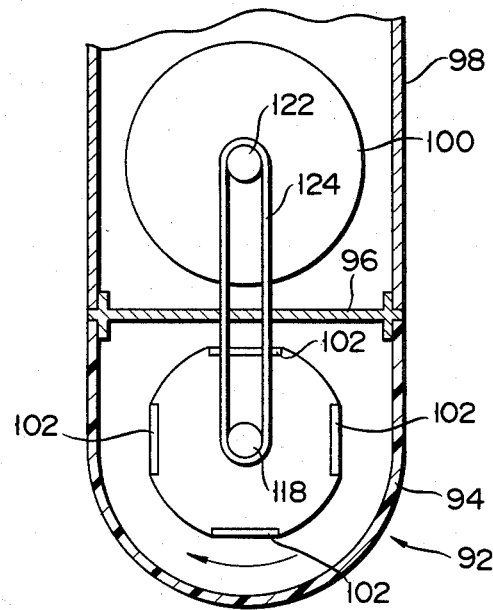

Reference numeral 92 in FIGS. 4 and 5 denotes a housing filled with acoustic liquid medium 93, such as water or glycol. Housing 92 comprises window member 94 and inner case 96. Window member 94 is made of plastic or rubber, and possesses ultrasonic transmission properties. Window member 94 is attached to inner case 96. Reference numeral 98 denotes an outer case for accommodating motor 100 and the like. Outer case 98 is attached to the end of inner case 96, on the side opposite to window member 94.

Four vibrators 102 and scanning mechanism 104 are arranged in housing 92. Vibrators 102 generate ultrasonic waves. A number of wires (not shown) are connected to vibrators 102. These wires provides ultrasonic pulses to vibrators 102 and echo signals therefrom, to an ultrasonic imaging apparatus. Scanning mechanism 104 includes columnar holder 106. Vibrators 102 are angularly separated from each other, on the edge of holder 106. Holder 106 is held by support shaft 108 at the axis of holder 106. Support shaft 108 extends outward from both ends of holder 106. One end of support shaft 108 is rotatably supported, via bearing 112, by frame 110 extending inside inner case 96. The other end of shaft 108 extends in through hole 114 formed in inner case 96, and is rotatably supported by case 96, via bearing 116. Pulley 118 is mounted on shaft 108 extending from case 96. Belt 124 is looped between pulley 118 and pulley 122 mounted on rotating shaft 120 of motor 100. Holder 106 is rotated upon rotation of motor 100, and vibrators 102 are rotated about shaft 108.

Seal member 126 is mounted in insertion hole 114 of inner case 96. Seal member 126 serves to seal a circular gap between case 96 and support shaft 108 in insertion hole 114.

Partition wall 128 is positioned inside housing 92 as to define first liquid medium chamber 130 and second liquid medium chamber 132 adjacent thereto. Chamber 130 accommodates vibrators 102 and scanning mechanism 104. Wall 128 is a funnel-shaped wall tapered toward chamber 132, that is to say, partition wall 128 has a portion, nearer central hole 134 thereof, which is separated more from vibrators 102. The distal end portion of shaft 108 is loosely inserted in central hole 134 in wall 128. Spiral groove 136 is formed in the peripheral surface of shaft 108, at a position corresponding to hole-formation surface 134a of partition wall 128.

Bubble guide pipe 138 extends outside inner case 96, and guides bubbles mixed in with the liquid medium into chamber 132 when the scanner is used in its normal operating position.

With the above arrangement, a patient, as the subject to be examined, lies on a bed. The ultrasonic radiation surface, i.e., the portions of window member 94 opposing vibrators 102, are directed along the vertical direction. Ultrasonic waves are generated by vibrators 102 in this state, vibrators 102 being rotated about shaft 118 upon rotation of motor 100, thereby enabling them to acquire ultrasonic information. In this condition, first and second liquid medium chambers 130 and 132 are located substantially at an identical level. For this reason, bubbles present in acoustic liquid medium 93 in chamber 130 are moved upward by buoyancy, and collect at the upper portion of chamber 130. When the scanner is not being used, it is turned through 90 degrees, to position chamber 130 below chamber 132. The bubbles which have been collected in chamber 130 are moved along the surface of partition wall 128 and soon arrive near hole 134, where buoyancy enables them to pass through a gap between rotating shaft 108 and hole-formation surface 134a of partition wall 128. In this case, if motor 100 is rotated, the bubbles are forcibly introduced into chamber 132, along spiral groove 136. The bubbles continue to move upward in chamber 132, and soon arrive near seal member 126. When the scanner is turned through 180 degrees, the bubbles in chamber 132 remain trapped at the corner of partition wall 128. When the scanner is then used once again, the bubbles are guided to supplementary chamber 140. Thus, for as long as the scanner continues its normal operations, the bubbles in chamber 132 or 140 will not return into chamber 130.

The same effect as in the first embodiment can be obtained by way of the above arrangement.

Supplementary chamber 140 need not be included in the scanning device of the present invention. In the third embodiment, the driving force of motor 100 is transmitted to support shaft 108, via belt 124. Alternatively, rotating shaft 120 of motor 100 may be coupled directly to support shaft 108.

A fourth embodiment of the present invention will now be described, with reference to FIGS. 6 to 8.

Figure 6:
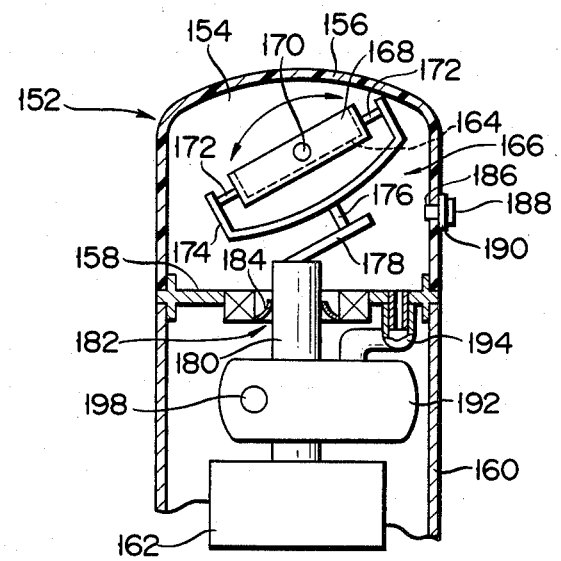

Reference numeral 152 in FIG. 6 denotes a housing filled with acoustic liquid medium 154, such as water or glycol. Housing 152 includes window member 156 and frame 158. Window member 156 comprises a plastic or rubber cylindrical member, open at one end. Window member 156 possesses ultrasonic transmission properties. The open end of window member 156 is attached to frame 158. Reference numeral 160 denotes a case for accommodating motor 162 and the like. Case 160 is attached to an end of frame 158, at the side opposite to window member 156.

Vibrator 164 and scanning mechanism 166 are accommodated in housing 152. Vibrator 164 generates ultrasonic waves. A lead wire (not shown) is connected to vibrator 164, and provides ultrasonic pulses to vibrator 164 and echo signals therefrom, to an ultrasonic imaging apparatus. Scanning mechanism 166 has holder 168 for holding vibrator 164. Two pairs of radial support shafts 170 and 172 extend from holder 168. One pair of support shafts 170 are rotatably supported by support frame 171 (FIG. 8) extending from frame 158. The other pair of support shafts 172 are rotatably supported by opposite ends of substantially U-shaped support arm 174. Rod 176 extends from the central portion of support arm 174. The distal end of rod 176 is connected to connecting member 178, by way of a ball bearing (not shown). Connecting member 178 is connected to rotating shaft 180 of motor 162. When rotating shaft 180 of motor 162 is rotated, holder 168 is pivotally reciprocated about support shaft 170.

Rotating shaft 180 of motor 162 is inserted in liquid medium chamber defining member 152, through insertion hole 182 formed in frame 158. Seal member 184 is mounted in hole 182 of frame 158, and serves to seal a circular gap between frame 158 and rotating shaft 180 in hole 182.

Figure 7:
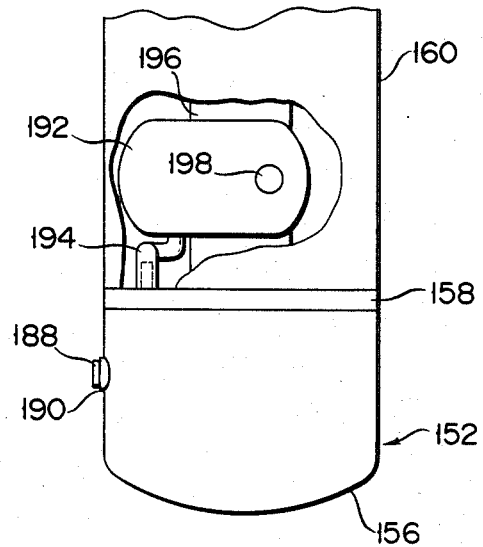
Figure 8:
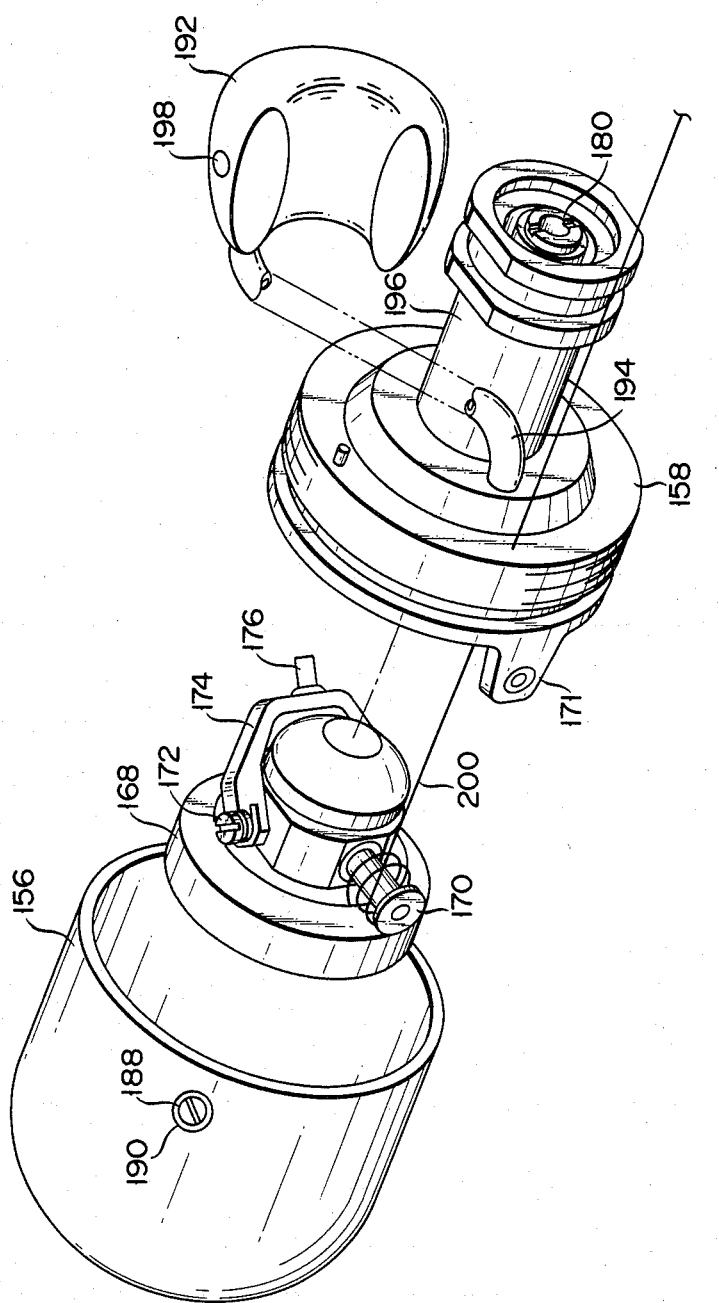

As is shown in FIGS. 6 to 8, air vent hole 186 is formed in the side surface of window member 156. Hole 186 can be sealed by air vent screw 188 and packing 190, and opened as required.

Sealed rubber bag 192 is arranged inside case 160, and communicates with housing 152, via rubber tube 194. Rubber bag 192 has an arcuated shape and is fitted on cylindrical portion 196 (FIGS. 7 and 8) of frame 158, through which rotating shaft 180 is inserted. Bag 192 has rubber stop 198, and is sealed thereby. A liquid can be injected into bag 192, through stop 198, using a syringe (not shown) capable of penetrating stop 198. After removing the cannula of syringe from stop 198, the liquid is sealed in bag 192.

As is shown in FIG. 8, lead wire 200 extends through holder 168, and is connected to vibrator 164. Lead wire 200 comprises a so-called coaxial cable having an integral sheath. A portion of lead wire 200 which extends from holder 168 is wound around and fixed to a rod (not shown) having a predetermined diameter (larger than that of support shaft 170). The wound portion is heated to about 100° C., and then curls by way of the thermal deforming of the sheath. The curled portion of lead wire 200 is loosely wound around support shaft 170.

With this arrangement, if bubbles form in housing 152, air vent screw 188 is removed from air vent hole 186, while hole 186 faces upward. The cannula (not shown) of a syringe filled with acoustic liquid medium 154 is inserted into rubber stop 198, for the injecting of the liquid medium thereinto. Therefore, bubbles having a smaller specific gravity than that of the liquid medium can be eliminated through upper air vent hole 186. Hole 186 is closed, and liquid medium 154 is injected from the cannula into bag 192. The internal pressure within housing 152 can be maintained at a sufficiently high positive pressure, by the inherent elastic contracting force exerted by rubber bag 192. Even if seal 184 is directed downward, as shown in FIG. 6, generation of subsequent bubbles can be adequately prevented. In addition, after the cannula is removed from stop 198, acoustic liquid medium 154 does not flow out. This is due to the elastic self-closing of rubber stop 198. At the same time, air is not introduced into housing 152.

Lead wire 200 is curled and loosely wound around support shaft 170, as is described above. Even if vibrator 168 sweeps back and forth at a rate of 30 times/- second, the resulting stress generated thereby does not act on wire 200. For this reason, wire 200 does not become electrically disconnected, and thus, the service life of scanning mechanism 166 can be prolonged. Lead wire 200 is not brought into contact with other components around support shaft 170, at the time of assembly of scanning mechanism 166, nor are coils of lead wire 200 brought into contact with each other.

A fifth embodiment of the present invention will now be described, with reference to FIG. 9.

Figure 9:
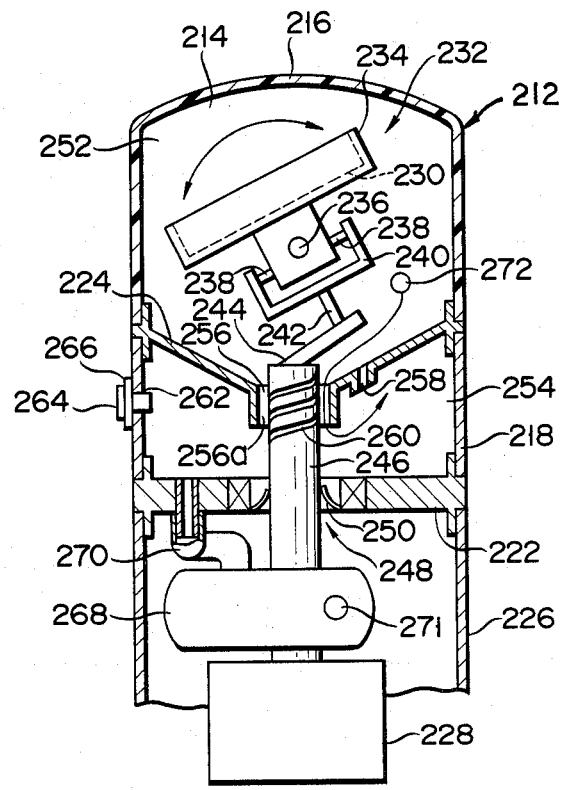
FIG. 9 is a sectional view showing a mechanical type ultrasonic scanner according to a fifth embodiment of the present invention.

Reference numeral 212 in FIG. 9 denotes a housing filled with acoustic liquid medium 214, such as water or glycol. Housing 212 includes window member 216, cylinder 218, and frame 220. Window member 216 comprises a plastic or rubber cylindrical member, open at one end. Window member 216 possesses ultrasonic transmission properties. One end of cylinder 218 is attached to the open end of window member 216, by way of partition wall 224 (to be described later). Frame 222 is attached to the other end of cylinder 218, on the side opposite to window member 216. Reference numeral 226 denotes a case for accommodating motor 228 and the like. Case 226 is attached to an end of frame 222, on the side opposite to cylinder 218.

Vibrator 230 and scanning mechanism 232 are arranged in housing 212. Vibrator 230 generates an ultrasonic wave. A lead wire (not shown) is connected to vibrator 230, and provides ultrasonic pulses to vibrator 230 and echo signals therefrom, to an ultrasonic imaging apparatus. Scanning mechanism 232 has holder 234 for holding vibrator 230. Two pairs of radial support shafts 236 and 238 extend from holder 234. One pair of support shafts 236 are rotatably supported by a support frame (not shown) extending from partition wall 224. The other pair of support shafts 238 are rotatably supported by opposite ends of substantially U-shaped support arm 240. Rod 242 extends from the central portion of support arm 240. The distal end of rod 242 is connected to connecting member 244, by way of a ball bearing (not shown). Connecting member 244 is connected to rotating shaft 246 of motor 228. When rotating shaft 246 of motor 228 is rotated, holder 234 is pivotally reciprocated about support shaft 236.

Rotating shaft 246 of motor 228 is inserted in housing 212, through insertion hole 248 formed in frame 222. Rotating shaft 246 extends along the axis of window member 216. Seal member 250 is mounted in insertion hole 248 of frame 222. Seal member 250 serves to seal a circular gap between frame 222 and rotating shaft 246 in hole 248.

Partition wall 224 is positioned inside housing 212 as to define first liquid medium chamber 252 and second liquid medium chamber 254 adjacent to chamber 252. Chamber 252 accommodates vibrator 230 and scanning mechanism 232. Partition wall 224 is a funnel-shaped wall tapered toward chamber 254, that is to say, partition wall 224 has a portion, nearer central hole 256 thereof, which is separated more from vibrator 230. Window member 216 and cylinder 218 are attached to the periphery of partition wall 224. The distal end of rotating shaft 246 is loosely inserted in central hole 256 of wall 224. Through hole 258 is formed in the wall 224, between central hole 256 and the peripheral portion of wall 224. Hole 258, together with the gap between hole-formation surface 256a and rotating shaft 246, constitutes a circulating path of acoustic liquid medium 214. Medium 214 flows, through the gap, from first liquid medium chamber 252 into second liquid medium chamber 254, and from chamber 254 to chamber 252, through hole 258. Spiral groove 260 is formed on the peripheral surface of rotating shaft 246, at a position opposite to hole formation surface 256a.

Air vent hole 262 is formed in the side surface of cylinder 218. Hole 262 is opened by air vent screw 264, and is sealed closed by packing 266 used in combination with screw 264.

Sealed rubber bag 268 is arranged in case 226, and communications with housing 212, via rubber tube 270. Rubber bag 268 has an arcuated shape and is fitted on rotating shaft 246. Bag 268 has rubber stop 270, and is sealed thereby. A liquid can be injected into bag 268, through stop 270, using a syringe (not shown) capable of penetrating stop 198. After the cannula of the syringe is removed from rubber stop 270, the liquid sealed in bag 268.

The operation of the mechanical type ultrasonic scanner having the above arrangement will be described below.

A patient as the subject to be examined lies on a bed. An ultrasonic radiation surface, i.e., the window member is directed in the vertical direction, and an ultrasonic wave is generated by vibrator 230, while being driven by motor 228. In this operating condition, first liquid medium chamber 252 is situated below second liquid medium chamber 254. Any bubbles 272 present in acoustic liquid medium 214 in chamber 252 are moved upward by buoyancy, and are guided along the surface of partition wall 224. The bubbles then arrive near hole 256, where buoyancy enables them to pass through the gap between rotating shaft 246 and hole-formation surface 256a of partition wall 224. If motor 228 is operated, bubbles 272 are forcibly introduced into chamber 254, along spiral groove 260. Medium 214, together with bubble 272, is guided to chamber 254. Simultaneously, medium 214 in chamber 254 flows into chamber 252. Bubbles 272, however, continue to move upward, and shortly arrive near seal member 250. Even if the mechanical scanner is turned through 180 degrees, bubbles 272 in chamber 254 remain trapped at the corner of partition wall 224. Thus, for as long as the scanner is in its normal operations, bubbles 272 in chamber 254 will not return into chamber 252.

When bubbles 272 are to be removed from second liquid medium chamber 254, air vent screw 264 is removed from air vent hole 262, while hole 262 faces upward. Medium 214 is injected via the cannula (not shown) of a syringe, through rubber stop 270. Therefore, bubbles 272, having a smaller specific gravity than that of medium 214, can be eliminated from air vent hole 262. After air vent hole 262 is closed, medium 214 is injected, under pressure, into bag 268. The internal pressure of housing 212 can be maintained at a proper positive pressure, by the inherent elastic contracting force exerted by rubber bag 268. Even if seal member 250 is directed downward, as shown in FIG. 9, generation of subsequent bubbles 272 can be adequately prevented. In addition, after the cannula of syringe is removed from stop 270, medium 214 does not flow out by the elastic self-closing of rubber stop 270, and air is not introduced into housing 212.

What is claimed is:

1. An ultrasonic scanner, comprising:
   a housing having first and second chambers holding an acoustic liquid, said first and second chambers being connected through a hole, and said first chamber having a window passing ultrasonic pulses;
   an ultrasonic transducer disposed in said first chamber;
   rotating shaft means, extending from said second to said first chamber through said hole, for stirring said liquid near the hole so that bubbles inside of said first chamber move to said second chamber through a gap between the hole and said rotating shaft means; and
   scanning means being connected with said rotating shaft means for giving said transducer scanning movement.

2. The apparatus according to claim 1, wherein said rotating shaft means proximate said hole has a spiral groove for forcibly introducing bubbles inside of said first chamber to said second chamber upon rotation of said rotation shaft.

3. The apparatus according to claim 2, wherein said second chamber has a pass for allowing the liquid to return to said first chamber.

4. The apparatus according to claim 1, wherein said first chamber has a funnel-shaped wall tapered toward said second chamber to gather the bubbles inside of said first chamber into said hole.

5. The apparatus according to claim 1, wherein said second chamber has a funnel-shaped wall tapered into said second chamber to prevent the bubbles trapped by said second chamber from returning to said hole when said apparatus is upside down.

6. The apparatus according to claim 1, wherein said apparatus further includes a elastic bag connected to said second chamber to pressurize the liquid.

7. An ultrasonic scanner, comprising:
   a housing holding an acoustic liquid and having a window thereon;
   a partition wall disposed inside of the housing to define first and second chambers, said partition wall having first and second holes;
   a rotating shaft extending from said second chamber to said first chamber through the first hole, said rotating shaft having a spiral groove proximate the first hole so that the liquid containing bubbles enters from said first chamber into said second chamber through a gap between said first hole and said first hole and said rotating shaft;
   ultrasonic transducer means, coupled to said rotating shaft, for transmitting ultrasonic pulses and receiving echoes of said pulses through the window; and
   transducer driver means, coupled to said rotating shaft, for causing said transducer to scan.

* * * * *